(12) United States Patent
Snow (10) Patent No.: US 7,217,240 B2
(45) Date of Patent: May 15, 2007

(54) HEART STABILIZER

(75) Inventor: Edward Ramsey Snow, Santa Barbara, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 254 days.

(21) Appl. No.: 10/892,386

(22) Filed: Jul. 14, 2004

(65) Prior Publication Data

US 2005/0043717 A1    Feb. 24, 2005

Related U.S. Application Data

(63) Continuation of application No. 09/870,331, filed on May 29, 2001, now Pat. No. 6,817,972, which is a continuation-in-part of application No. 09/411,442, filed on Oct. 1, 1999, now Pat. No. 6,936,001.

(51) Int. Cl.
*A61F 13/00* (2006.01)
*A61B 1/32* (2006.01)

(52) U.S. Cl. ............ 600/37; 600/215; 600/222

(58) Field of Classification Search ............ 600/37, 600/201, 210, 215, 222, 227, 228, 235; 128/897–898
See application file for complete search history.

(56) References Cited

U.S. PATENT DOCUMENTS

| | | |
|---|---|---|
| 977,825 A | 12/1910 | Murphy |
| 3,171,549 A | 3/1965 | Orloff |
| 3,280,991 A | 10/1966 | Melton et al. |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |

(Continued)

FOREIGN PATENT DOCUMENTS

DE    G 9204118.3    7/1992

(Continued)

OTHER PUBLICATIONS

ABSTRACT of a presentation "3-D Vision Technology Applied to Advanced Minimally Invasive Surgery Systems" given at the 3rd World Congress of Endoscopic Surgery in Bordeaux, (Jun. 18-20, 1992), entitled "Session 15/3" (1 page total).

(Continued)

*Primary Examiner*—John P. Lacyk (57) ABSTRACT

A heart stabilizer that may include a wrist which couples an end effector to a first linkage. The end effector and wrist may be inserted through an incision in the chest of a patient to assist in performing a minimally invasive coronary procedure. The wrist provides dexterity so that the end effector can be placed on the heart to stabilize the same. The end effector may include a pair of paddles that are moved between open and closed positions by a pair of manually actuated levers. The paddles may have cleats that allow sutures to be attached to the stabilizer during a minimally invasive procedure.

9 Claims, 11 Drawing Sheets

U.S. PATENT DOCUMENTS

| | | |
|---|---|---|
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,635,479 A | 1/1987 | Salisbury, Jr. et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Andersson et al. |
| 4,815,450 A | 3/1989 | Patel |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,046,375 A | 9/1991 | Salisbury, Jr. et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,442,728 A | 8/1995 | Kaufman et al. |
| 5,443,484 A | 8/1995 | Kirsch et al. |
| 5,445,166 A | 8/1995 | Taylor |
| 5,451,924 A | 9/1995 | Massimino et al. |
| 5,455,766 A | 10/1995 | Schaller et al. |
| 5,458,547 A | 10/1995 | Teraoka et al. |
| 5,458,574 A | 10/1995 | Machold et al. |
| 5,476,010 A | 12/1995 | Fleming et al. |
| 5,490,117 A | 2/1996 | Oda et al. |
| 5,490,843 A | 2/1996 | Hildwein et al. |
| 5,506,912 A | 4/1996 | Nagasaki et al. |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,718,038 A | 2/1998 | Takiar et al. |
| 5,727,569 A | 3/1998 | Benetti et al. |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,766,126 A | 6/1998 | Anderson |

| | | |
|---|---|---|
| 5,776,126 A | 7/1998 | Wilk et al. |
| 5,779,623 A | 7/1998 | Bonnell |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,827,319 A | 10/1998 | Carlson et al. |
| 5,836,869 A | 11/1998 | Kudo et al. |
| 5,844,824 A | 12/1998 | Newman et al. |
| 5,855,583 A | 1/1999 | Wang et al. |
| 5,859,934 A | 1/1999 | Green |
| 5,860,995 A | 1/1999 | Berkelaar |
| 5,865,730 A | 2/1999 | Fox et al. |
| 5,876,325 A | 3/1999 | Mizuno et al. |
| 5,878,193 A | 3/1999 | Wang et al. |
| 5,882,206 A | 3/1999 | Gillio |
| 5,887,121 A | 3/1999 | Funda et al. |
| 5,888,190 A | 3/1999 | Meyer et al. |
| 5,894,843 A | 4/1999 | Benetti et al. |
| 5,898,599 A | 4/1999 | Massie et al. |
| 5,904,702 A | 5/1999 | Ek et al. |
| 5,906,630 A | 5/1999 | Anderhub et al. |
| 5,911,036 A | 6/1999 | Wright et al. |
| 5,920,395 A | 7/1999 | Schultz |
| 5,931,832 A | 8/1999 | Jensen |
| 5,950,629 A | 9/1999 | Taylor et al. |
| 5,951,475 A | 9/1999 | Gueziec et al. |
| 5,951,587 A | 9/1999 | Qureshi et al. |
| 5,954,731 A | 9/1999 | Yoon |
| 5,957,902 A | 9/1999 | Teves |
| 5,980,782 A | 11/1999 | Hershkowitz et al. |
| 5,984,932 A | 11/1999 | Yoon |
| 6,024,695 A | 2/2000 | Taylor et al. |
| 6,036,641 A | 3/2000 | Taylor et al. |
| 6,063,021 A | 5/2000 | Hossain et al. |
| 6,080,181 A | 6/2000 | Jensen et al. |
| 6,102,854 A | 8/2000 | Cartier et al. |
| 6,106,511 A | 8/2000 | Jensen |
| 6,113,534 A | 9/2000 | Koros et al. |
| 6,120,433 A | 9/2000 | Mizuno et al. |
| 6,132,368 A | 10/2000 | Cooper |
| 6,201,984 B1 | 3/2001 | Funda et al. |
| 6,223,100 B1 | 4/2001 | Green |
| 6,226,566 B1 | 5/2001 | Funda et al. |
| 6,231,526 B1 | 5/2001 | Taylor et al. |
| 6,246,200 B1 | 6/2001 | Blumenkranz et al. |
| 6,248,062 B1 | 6/2001 | Adler et al. |
| 6,259,806 B1 | 7/2001 | Green et al. |
| 6,290,644 B1 | 9/2001 | Green, II et al. |
| 6,306,146 B1 | 10/2001 | Dinkler |
| 6,315,718 B1 | 11/2001 | Sharratt |
| 6,331,157 B2 | 12/2001 | Hancock |
| 6,331,181 B1 | 12/2001 | Tierney et al. |
| 6,346,072 B1 | 2/2002 | Cooper |
| 6,364,888 B1 | 4/2002 | Nieneyer et al. |
| 6,371,906 B1 | 4/2002 | Borst et al. |
| 6,371,952 B1 | 4/2002 | Madhani et al. |
| 2002/0014567 A1 | 2/2002 | King et al. |
| 2002/0045888 A1 | 4/2002 | Ramans et al. |

FOREIGN PATENT DOCUMENTS

| | | |
|---|---|---|
| DE | 4310842 C2 | 1/1995 |
| EP | 0239409 A1 | 9/1987 |
| EP | 0424687 A1 | 5/1991 |
| EP | 0776738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

ABSTRACT of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).

ABSTRACT of a presentation "Concept and Experimental Application of a Surgical Robotic System the Steerable MIS Instrument SMI" given at the 3rd World Congress of Endoscopic Surgery in Bordeaux, Jun. 18-20, 1992 (1 page total).

ABSTRACT of a presentation given at the 3rd World Congress of Endoscopic Surgery in Bordeaux (Jun. 18-20, 1992), entitled "Session 15/2" (1 page total).

ABSTRACT of a presentation given at the 3rd World Congress of Endoscopic Surgery in Bordeaux (Jun. 18-20, 1992), entitled "Session 15/4" (1 page total).

ABSTRACT of a presentation given at the 3rd World Congress of Endoscopic Surgery in Bordeaux (Jun. 18-20, 1992), entitled "Session 15/5" (1 page total).

ABSTRACT of a presentation given at the 3rd World Congress of Endoscopic Surgery in Bordeaux (Jun. 18-20, 1992), entitled "Session 15/1" (1 page total).

Alexander, III, "A Survey Study of Teleoperators, Robotics, and Remote Systems Technology," Remotely Manned Systems—Exploration and Operation in Space, California Institute of Technology 1973, pp. 449-458.

Alexander, III, "Impacts of Telemation on Modern Society," On the Theory and Practice of Robots and Manipulators vol. II, 1974, pp. 121-136.

Bejczy, "Controlling Remote Manipulators through Kinesthetic Coupling," Computers in Mechanical Engineering 1983, pp. 48-60.

Besant et al., Abstract of a presentation "Camera Control for Laparoscopic Surgery by Speech-Recognizing Robot: Constant Attention and Better Use of Personnel," given at the 3rd World Congress of Endoscopic Surgery in Bordeaux, Jun. 18-20, 1992 (1 page total).

Charles et al., "Design of a Surgeon-Machine Interface for Teleoperated Microsurgery," IEEE 1989 (3 pages total).

Colgate, "Power and Impedance Scaling in Bilateral Manipulation," IEEE, 1991, pp. 2292-2297.

Corcoran, "Robots for the Operating Room," The New York Times, Sunday Jul. 19, 1992, Section 3, Page 9, Column 1 (2 pages total).

Das et al., "Kinematic Control and Visual Display of Redundant Teleoperators," IEEE 1989 pp. 1072-1077.

Dolan et al., "A Robot in an Operating Room: A Bull in a China Shop," IEEE, 1987, pp. 1096-1097.

Gayed et al., "An Advanced Control Micromanipulator for Surgical Applications," Systems Science vol. 13, 1987, pp. 23-34.

Green et al., Abstract of a presentation "Telepresence: Advanced Teleoperator Technology for Minimally Invasive Surgery," given at "Medicine meets virtual reality" symposium in San Diego, Jun. 4-7, 1992 (20 pages total).

Green et al., Abstract of a presentation "Telepresence: Advanced Teleoperator Technology for Minimally Invasive Surgery," given at the 3rd World Congress of Endoscopic Surgery in Bordeaux, Jun. 18-20, 1992 (2 pages total).

Guerrouad et al., "S.M.O.S.: Stereotaxical Microtelemanipulator for Ocular Surgery," IEEE, 1989, pp. 879-880.

Inque et al., "Six-axis Bilateral Control of an Articulated Slave Manipulator Using a Cartesian Master Manipulator," Advanced Robotics, 4, No. 2, 1990, pp. 139-150.

Kazerooni, "Human/Robot Interaction via the Transfer of Power and Information Signals—Part I: Dynamics and Control Analysis," IEEE, 1989, pp. 1632-1640.

Kazerooni, "Human/Robot Interaction via the Transfer of Power and Information Signals—Part II: An Experimental Analysis," IEEE, 1989, pp. 1641-1647.

Krishnan et al., Abstract of a presentation "Design Considerations of a New Generation Endoscope Using Robotics and Computer Vision Technology," given at the 3rd World Congress of Endoscopic Surgery in Bordeaux, Jun. 18-20, 1992 (1 page total).

Lavallee, "A New System for Computer Assisted Neurosurgery," IEEE, 1989, vol. 11, pp. 926-927.

Mair, Industrial Robotics, Prentice Hall, 1988, pp. 41-43, 49-50, 54, 203-209.

Majima et al., "On a Micro-Manipulator for Medical Application—Stability Consideration of its Bilateral Controller," Mechatronics, 1991, pp. 293-309.

Preising et al., "A Literature Review: Robots in Medicine," IEEE, Jun. 1991, pp. 13-22 & 71.

Rasor et al., "Endocorporeal Surgery Using Remote Manipulators," Remotely Manned Systems—Exploration and Operation in Space, California Institute of Technology 1973, pp. 483-492.

Sabatini et al., "Force Feedback-Based Telemicromanipulation for Robot Surgery on Soft Tissues," IEEE, 1989, pp. 890-891.

Taubes, "Surgery in Cyberspace," Discover Mangazine, Dec. 1994, pp. 85-92.

Taylor et al., "Taming the Bull: Safety in a Precise Surgical Robot," IEEE, 1991, pp. 865-871.

Tejima, "A New Microsurgical Robot System for Corneal Transplantation," Precision Machinery, 1988 vol. 2, pp. 1-9.

Tendick et al., "Analysis of the Surgeon's Grasp for Telerobotic Surgical Manipulation," IEEE, 1989, pp. 914-915.

Thring, "Robots and Telechirs: Manipulator with Memory: Remote Manipulators: Machine Limbs for the Handicapped," Wiley & Sons, 1983 (26 pages total).

TRANSCRIPT of a video presented by SRI at the 3rd World Congress of Endoscopic Surgery in Bordeaux on Jun. 18-20, 1992, in Washington on Apr. 9, 1992, and in San Diego, CA on Jun. 4-7, 1992 entitled "Telepresence Surgery—The Future of Minimally Invasive Medicine" (3 pages total).

Trevelyan et al., "Motion Control for a Sheep Shearing Robot," Proceedings of the 1st International Symposium on Robotics Research, MIT, Cambridge, Massachusetts, USA, 1983, pp. 175-190.

Vibet, "Properties of Master-Slave Robots," Motor-con, 1987, pp. 309-314.

Wolf et al., "Student Reference Manual for Electronic Instrumentation Laboratories," Prentice Hall, New Jersey 1990, pp. 498-499.

HEART STABILIZER

CROSS-REFERENCES TO RELATED APPLICATIONS

The present application is a continuation of U.S. Patent application Ser. No. 09/870,331, filed May 29, 2001, now U.S. Pat No. 6,817,972, which was a continuation-in-part of U.S. Patent application Ser. No. 09/411,442, filed Oct. 1, 1999, now U.S. Pat No. 6,936,001, the full disclosures of which are incorporated by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

Field of the Invention

The present invention relates to an articulate heart stabilizer.

Blockage of a coronary artery may deprive the heart of blood and oxygen required to sustain life. The blockage may be removed with medication or by an angioplasty. For severe blockage a coronary artery bypass graft (CABG) is performed to bypass the blocked area of the artery. CAEG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform a minimally invasive CABG procedure. The procedure is performed with instruments that are inserted through small incisions in the patient's chest. The instruments are controlled by robotic arms. Movement of the robotic arms and actuation of the instrument end effectors are controlled by the surgeon through a pair of handles and a foot pedal that are coupled to an electronic controller. When performing a coronary procedure it is desirable to stabilize the heart. A heart stabilizer can be provided to limit the movement of the heart at the surgical site to reduce the complexity of performing the coronary procedure. To date there has not been developed a heart stabilizer that can be used in a minimally invasive procedure. A minimally invasive heart stabilizer must have enough dexterity to be maneuvered within the chest cavity of the patient.

There have been developed articulate retractors that are used in open-heart surgery. The articulate retractors have a pair of wrist joints that allow pivotally movement of a retractor relative to a handle shaft. The joints are spatially separated such that manipulation of the retractor is cumbersome and would be impractical for use in a minimally invasive procedure. It would therefore be desirable to provide a heart stabilizer that can be used in a minimally invasive procedure.

BRIEF SUMMARY OF THE INVENTION

One embodiment of the present invention is a heart stabilizer that may include a wrist, which couples an end effector to a first linkage. The end effector and wrist may be inserted through an incision in the chest of a patient to assist in performing a minimally invasive coronary procedure. The end effector may be manually actuated by moving a lever of the stabilizer.

DETAILED DESCRIPTION OF THE INVENTION

Figure 1:
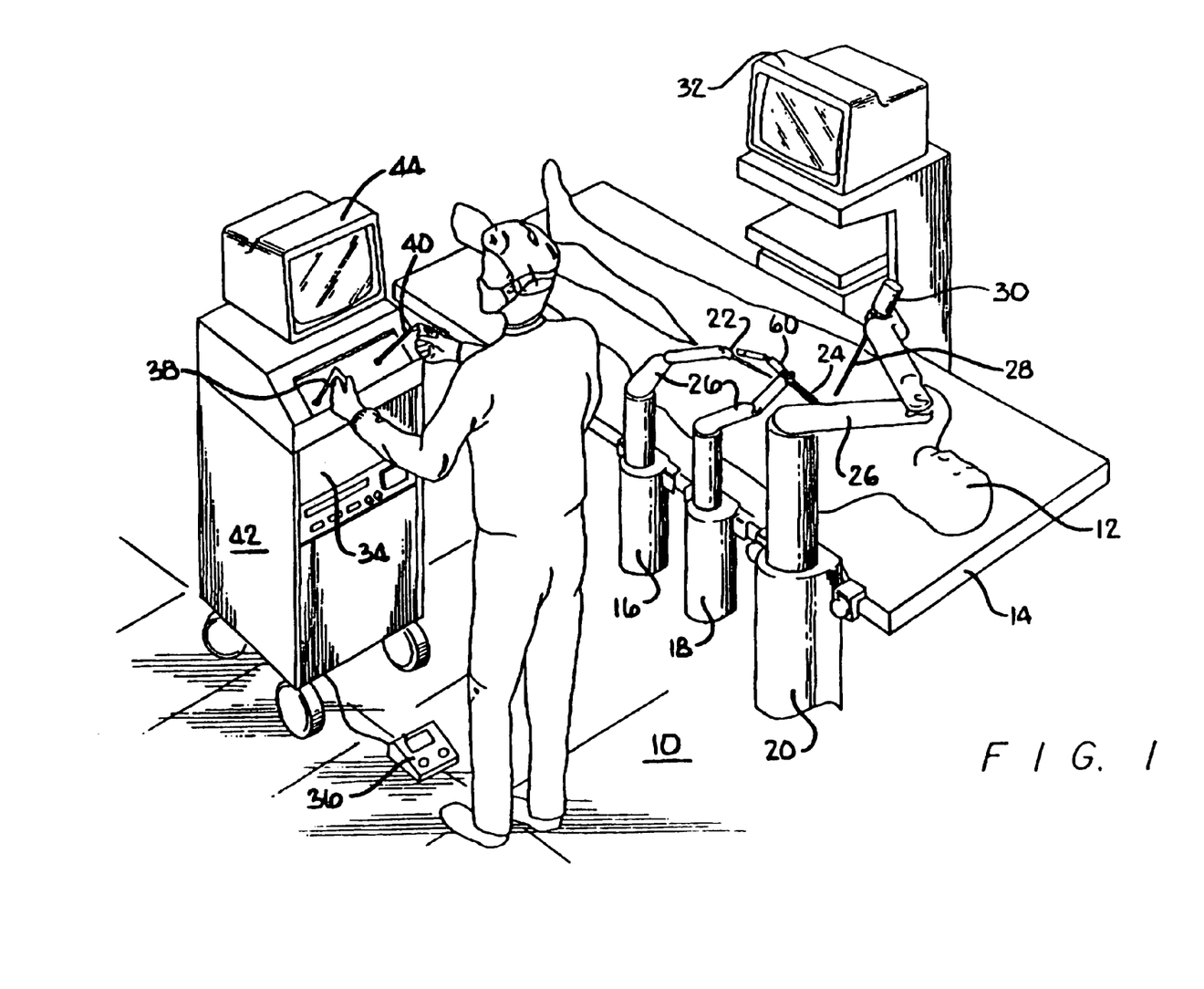
FIG. 1 is a perspective view of an embodiment of a minimally invasive surgical system of the present invention.

Referring to the drawings more particularly by reference numbers, FIG. 1 shows a system 10 that can perform minimally invasive surgery. In the preferred embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels. The system 10 can be used to perform a procedure on a patient 12 that is typically lying on an operating table 14. Mounted to the operating table 14 is a first articulate arm 16, a second articulate arm 18 and a third articulate arm 20. The articulate arms 16, 18 and 20 are preferably mounted to the table 14 so that the arms are at a same reference plane as the patient. Although three articulate arms are shown and described, it is to be understood that the system may have any number of arms.

The first and second articulate arms 16 and 18 each have a surgical instrument 22 and 24, respectively, coupled to a robotic arm 26, respectively. The third 25 articulate arm 20 has an endoscope 28 that is held by a robotic arm 26. The instruments 22 and 24, and endoscope 28 are inserted through incisions cut into the skin of the patient. The endoscope has a camera 30 that is coupled to a television monitor 32 which displays images of the internal organs of the patient. The first 16, second 18, and third 20 articulate arms are coupled to a controller 34 which can control the movement of the arms. The controller 34 is connected to an input device 36 such as a foot pedal that can be operated by a surgeon to move the location of the endoscope 28. The surgeon can view a different portion of the patient by depressing a corresponding button(s) of the pedal 36. The controller 34 receives the input signal(s) from the foot pedal 36 and moves the robotic arm 26 and endoscope 28 in accordance with the input commands of the surgeon. The robotic arms 26 may be devices that are sold by the assignee of the present invention, Computer Motion, Inc. of Goleta, Calif., under the trademark AESOP. The system is also described in U.S. Pat. No. 5,657,429 issued to Wang et al., which is hereby incorporated by reference. Although a foot pedal 36 is shown and described, it is to be understood that the system may have other input means such as a hand controller, or a speech recognition interface.

The instruments 22 and 24 of the first 16 and second 18 articulate arms, respectively, are controlled by a pair of master handles 38 and 40 that can be manipulated by the surgeon. The handles 38 and 40, and arms 16 and 18, have a master-slave relationship so that movement of the handles 38 and 40 produces a corresponding movement of the surgical instruments. The handles 38 and 40 may be mounted to a portable cabinet 42. A second television monitor 44 may be placed onto the cabinet 42 and coupled to the endoscope 28 so that the surgeon can readily view the internal organs of the patient. The handles 38 and 40 are also coupled to the controller 34. The controller 34 receives input signals from the handles 38 and 40, computes a corresponding movement of the surgical instruments, and provides output signals to move the robotic arms and instruments. The entire system may be a product marketed by Computer Motion under the trademark Zeus. The operation of the system is also described in U.S. Pat. No. 5,762,458 issued to Wang et al. and assigned to Computer Motion, which is hereby incorporated by reference.

The system may also include a heart stabilizer 60 that is used to perform minimally invasive coronary procedures. The stabilizer 60 is typically inserted through an incision of the patient's chest. The stabilizer 60 can be held by a robotic arm or a static structure (not shown).

Figures 2, 3, 4:
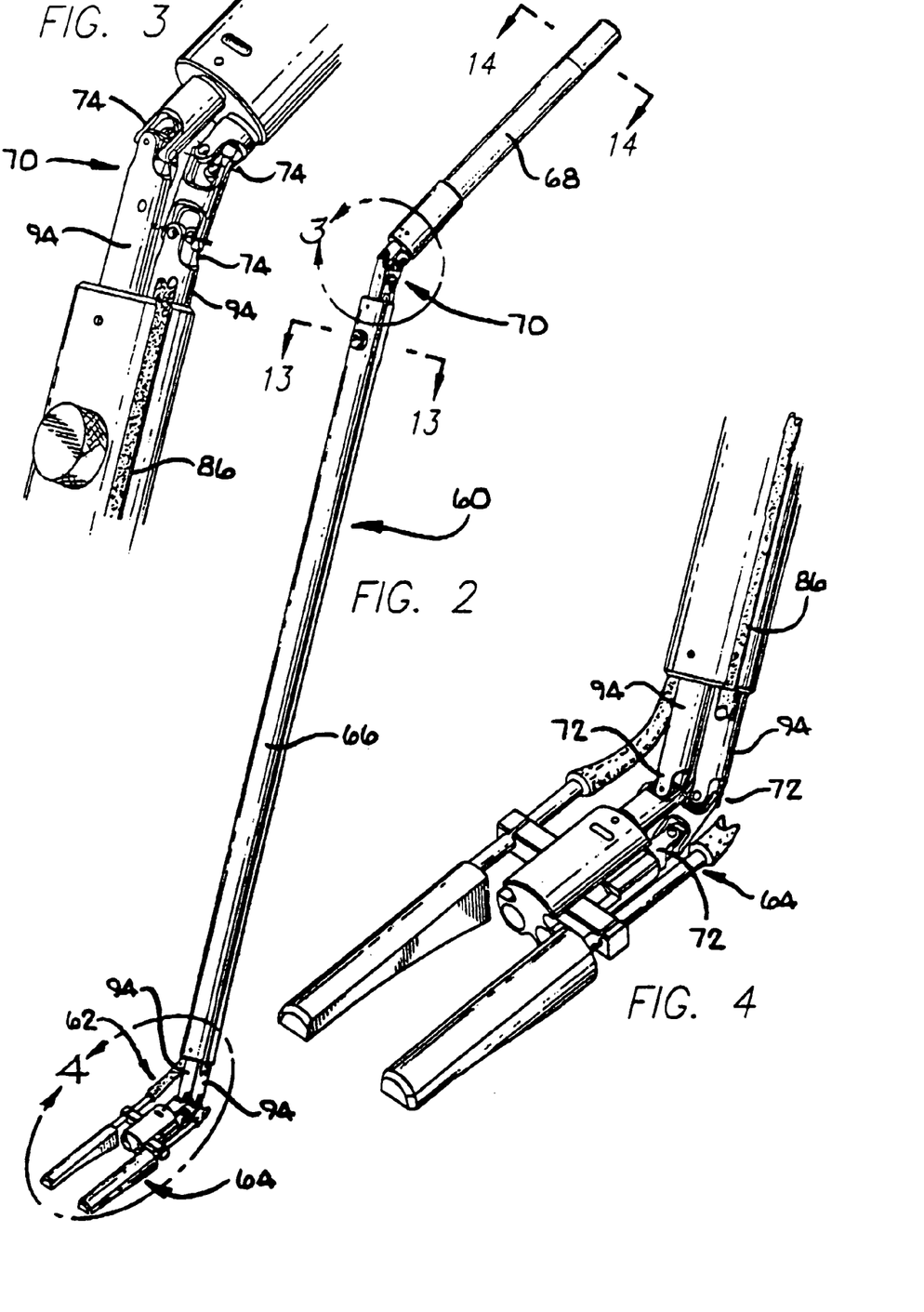
FIG. 2 is a perspective view of an embodiment of a heart stabilizer of the present invention.
FIG. 3 is an enlarged view of an elbow of the heart stabilizer.
FIG. 4 is an enlarged view of an end effector of the heart stabilizer.
Figure 8:
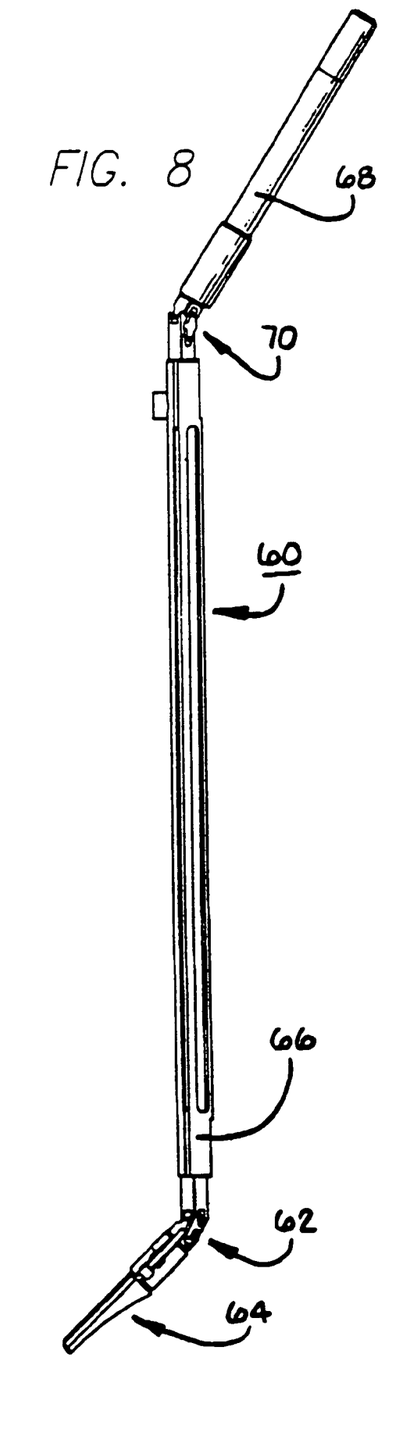
FIG. 8 is a side view of the heart stabilizer.
Figure 9:
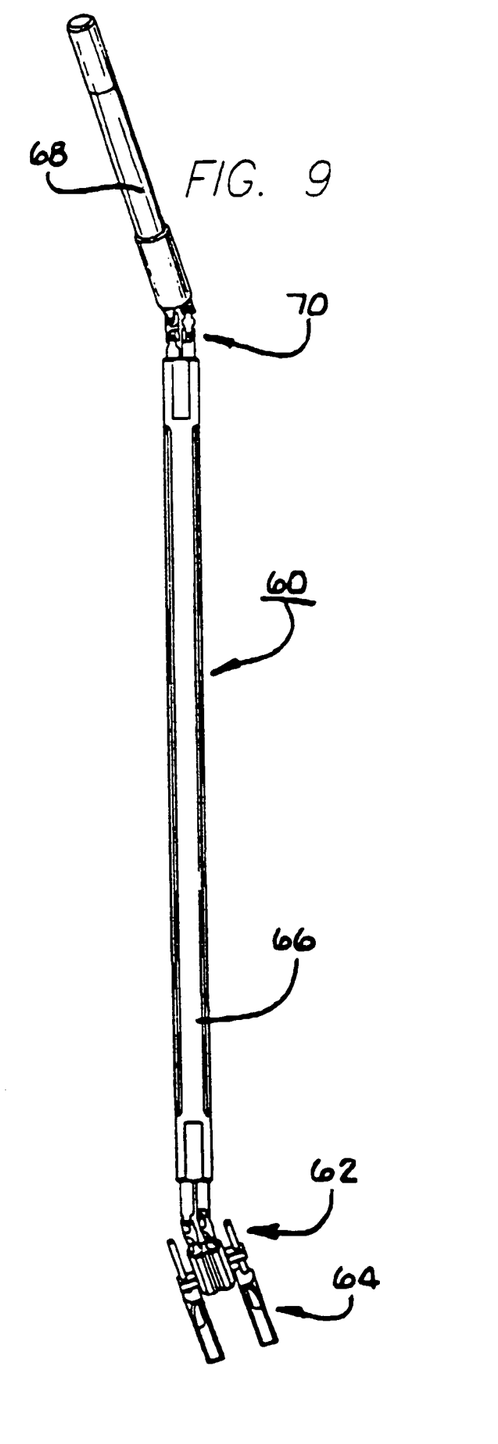
FIG. 9 is a bottom view of the heart stabilizer.

FIGS. 2–14 show an embodiment of a heart stabilizer 60. Referring to FIGS. 2, 8 and 9, the heart stabilizer 60 may comprise a wrist 62 that couples an end effector 64 to a first linkage 66. The wrist 62 allows the end effector 64 to be moved relative to the first linkage 66. The first linkage 66 may be coupled to a second linkage 68 by an elbow 70. The elbow 70 allows the first linkage 66 to be moved relative to the second linkage 68. The wrist 62 and elbow 70 allow the end effector 64 to be accurately located within the chest cavity of a patient. Each linkage 66 and 68 may be a cannula with an inner longitudinal channel.

As shown in FIGS. 3 and 4 the elbow 70 and wrist 62 may have a plurality of universal joints 72 and 74, respectively, that provide three degrees of freedom. At least two universal joints 72 of the wrist 62 may pivot about the same plane to minimize the relative movement of one joint pivot point relative to another joint pivot point. Relative pivot point movement can increase the complexity of positioning the end effector 64. Likewise, two or more universal joints 74 of the elbow 70 can pivot about the same plane.

Referring to FIGS. 5, 6, 7, 10, 11 and 12, the end effector 64 may have a pair of paddles 76 that can move relative to a gear housing 78. Each paddle 76 may have an opening 80 that is in fluid communication with a rigid tube 82. Each rigid tube 82 may be connected to a flexible tube 84. The flexible tubes 84 may be connected to a source of vacuum (not shown) that can create a vacuum pressure at the openings 80. The flexible tubes 84 can be routed along channels 86 of the first linkage 66, as shown in FIGS. 2 and 4, to minimize the profile of the stabilizer 60. Although suction paddles are shown and described, it is to be understood that the heart stabilizer 60 may be used without a suction system. Each rigid tube 84 may be connected to a gear rack 88. Each gear rack 88 can move within corresponding channels 90 of the gear housing 78. The gear racks 90 may be coupled to corresponding pinion gears 92 attached to two of the universal joints 72 of the wrist 62.

Figure 5:
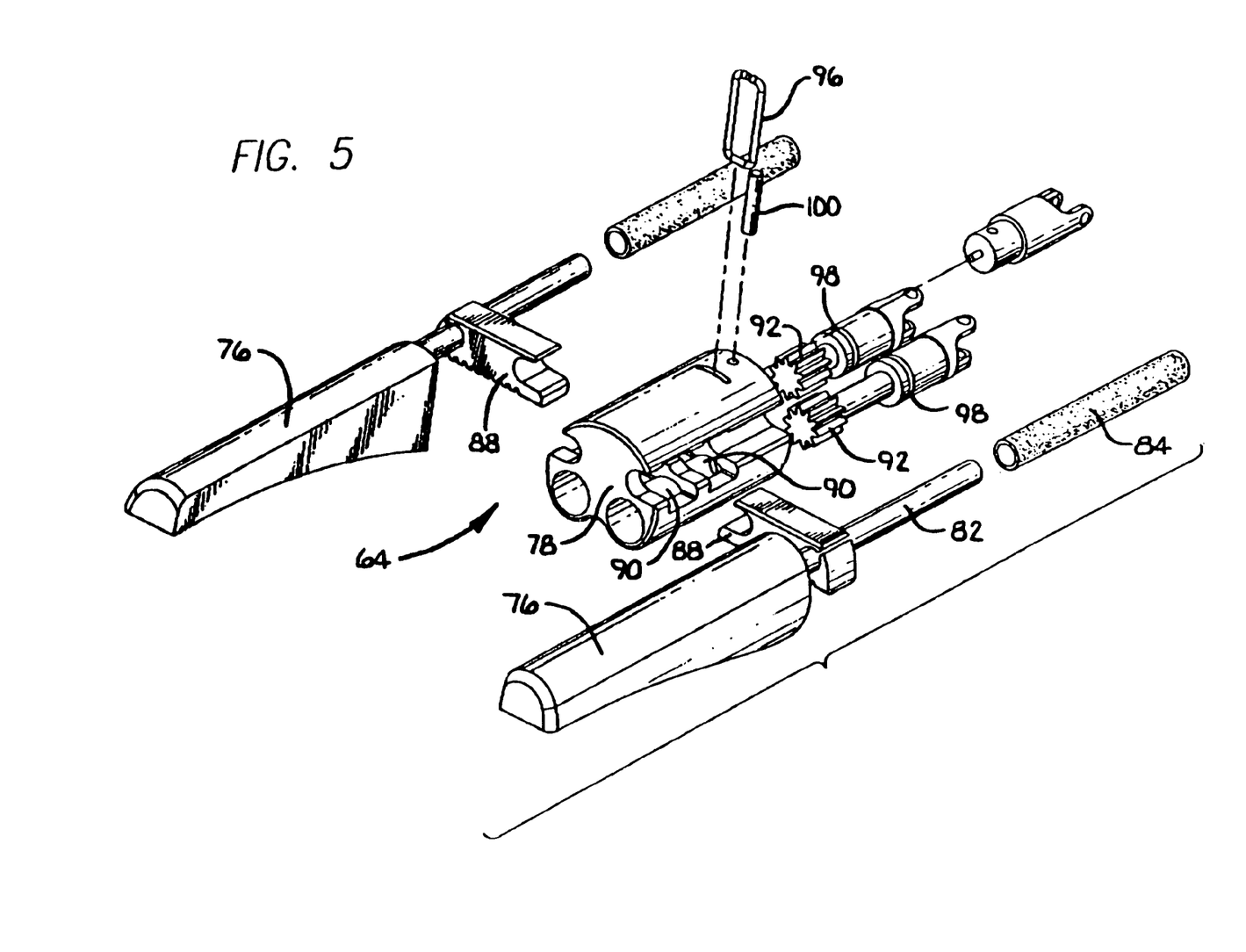
FIG. 5 is an exploded view of the end effector.
Figure 6:
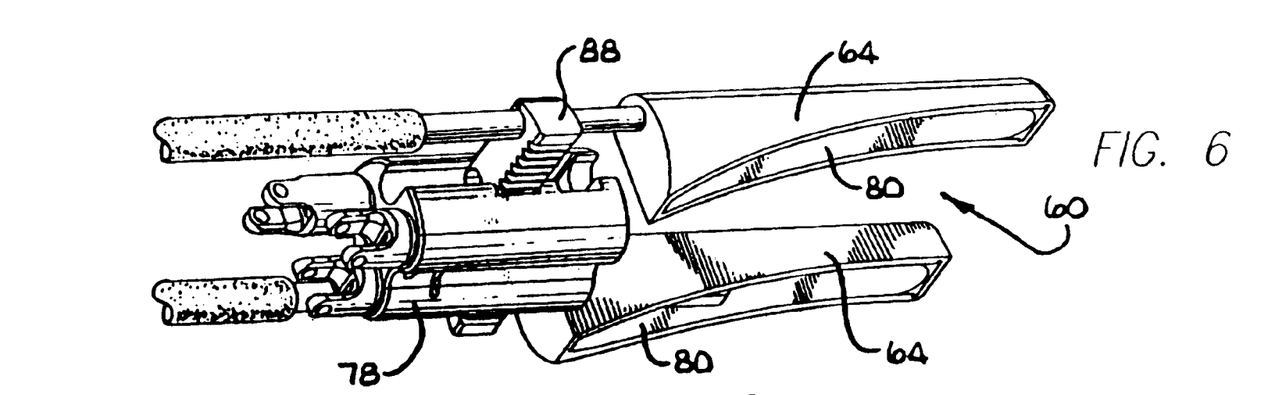
FIG. 6 is a bottom perspective view of the end effector.
Figure 7:
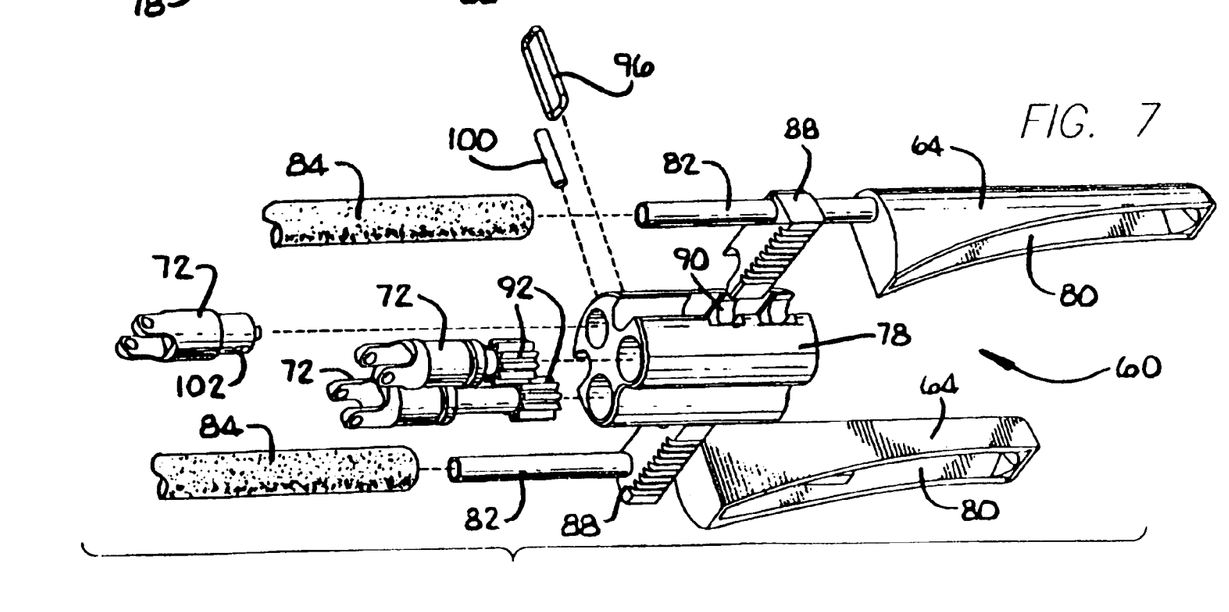
FIG. 7 is a bottom exploded view of the end effector.
Figures 10, 12:
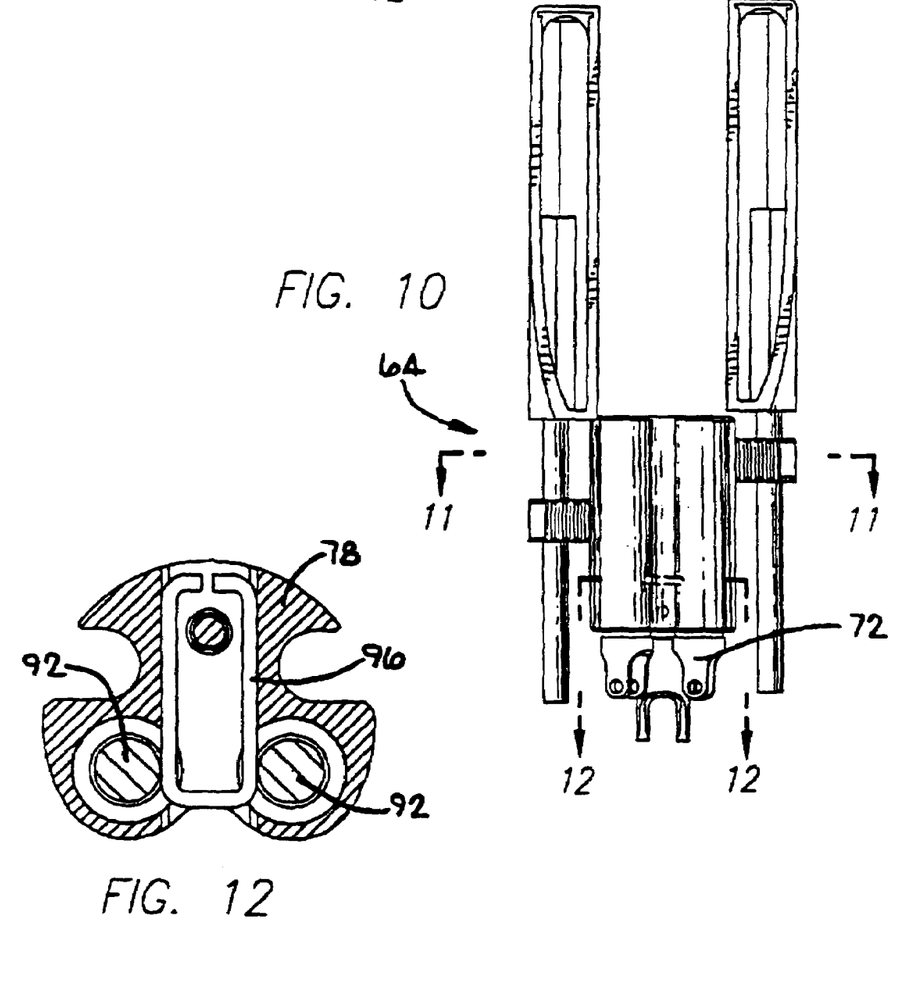
FIG. 10 is a bottom view of the end effector.
FIG. 12 is a sectional view taken at line 12—12 of FIG. 10.
Figure 11:
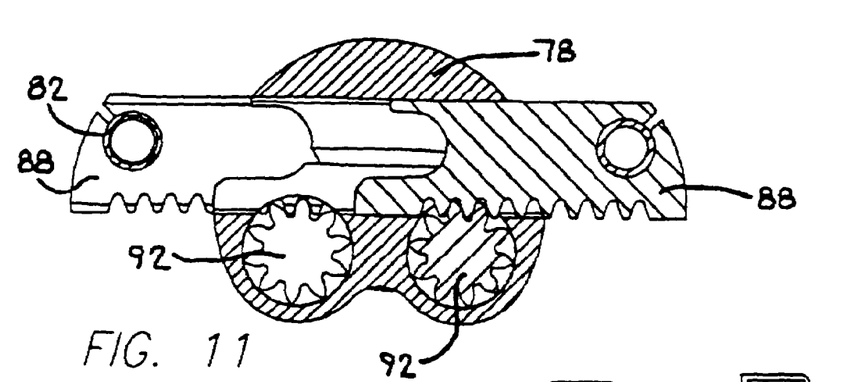
FIG. 11 is a sectional view taken at line 11—11 of FIG. 10.

The universal joints 72 may be connected to a pair of drive shafts 94 that extend through the first linkage 66 as shown in FIGS. 2, 3 and 4. Rotation of the drive shafts 94 will rotate the pinion gears 92 and translate the corresponding gear racks 88 and paddles 76 in an inward or outward direction. The movement of the paddles 76 occurs without disturbing the relative position of the end effector 64 to the first linkage 66. As shown in FIGS. 5, 7 and 12, the end effector 64 may include a spring clip 96 that is inserted into corresponding annular grooves 98 of the pinion gears 92 and captures the gears 92 within the gear housing 78. The end effector 64 may also have a pin 100 that is inserted into a corresponding aperture 102 of the other universal joint 72 to capture the joint 72 within the gear housing 78.

Figure 13:
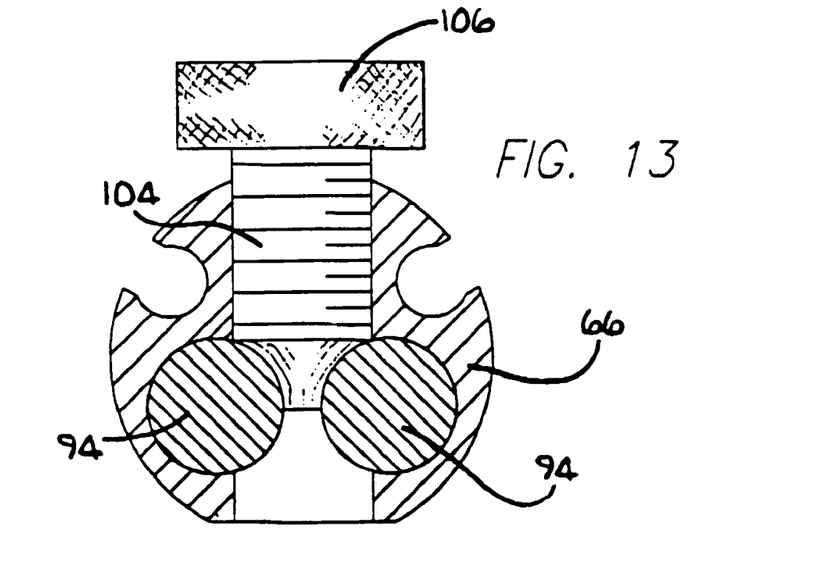
FIG. 13 is a sectional view taken at line 13—13 of 25 FIG. 2.

As shown in FIG. 13, the heart stabilizer 60 may include a locking pin 104 that can be pressed into the drive shafts 94 to prevent rotation of the shafts 94. Impeding shaft rotation locks the position of the wrist 62, elbow 70 and paddles 76. A surgeon may lock and unlock the wrist 62, elbow 70 and paddles 76 by rotating a head 106 of the pin 104.

Figure 14:
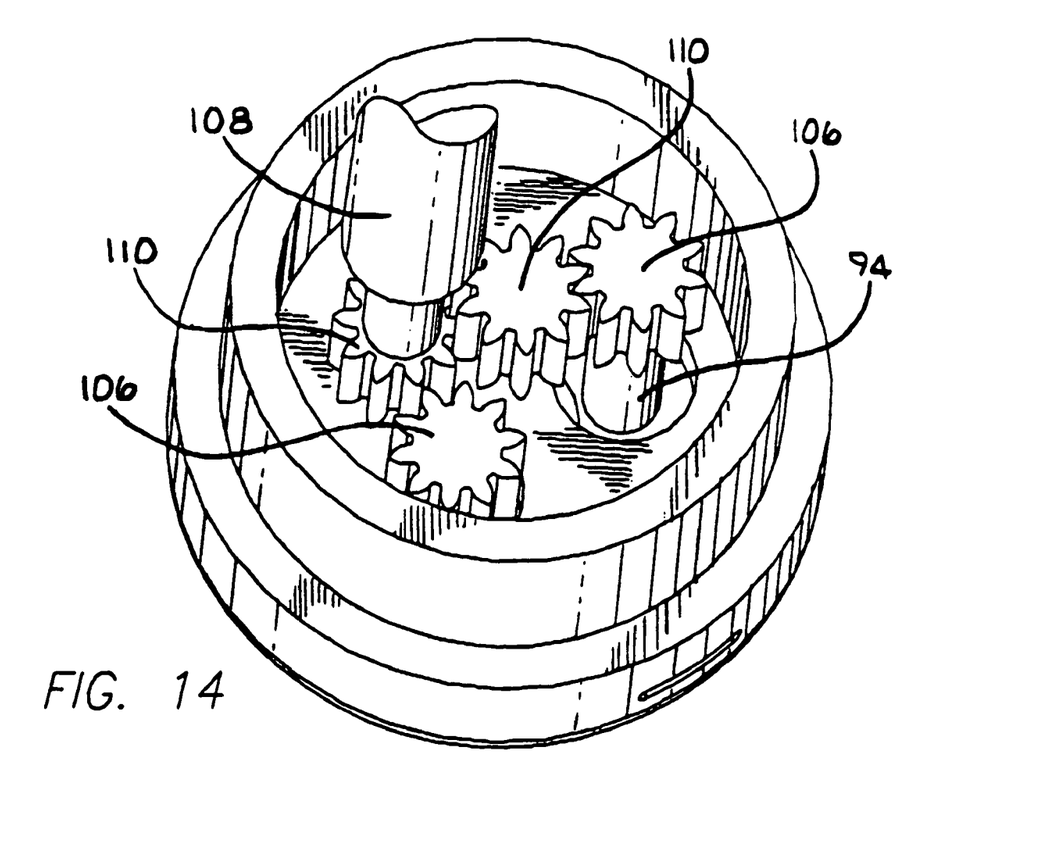
FIG. 14 is a sectional view taken at line 14—14 FIG. 2.

As shown in FIG. 14, each drive shaft 94 may have a pinion gear 106 that is coupled to an output shaft 108 of a motor (not shown) by a pair of coupling gears 110. Rotation of the output shaft 108 rotates the drive shafts and moves the paddles 76. The motor is preferably reversible so that the paddles 76 can be moved inward or outward. The motor may be connected to the controller 34 and foot pedal 36 shown in FIG. 1. The surgeon can move the paddles 76 inward or outward by depressing a corresponding switch(es) of the foot pedal 36. Alternatively, the motor can be actuated through voice recognition.

Figure 15:
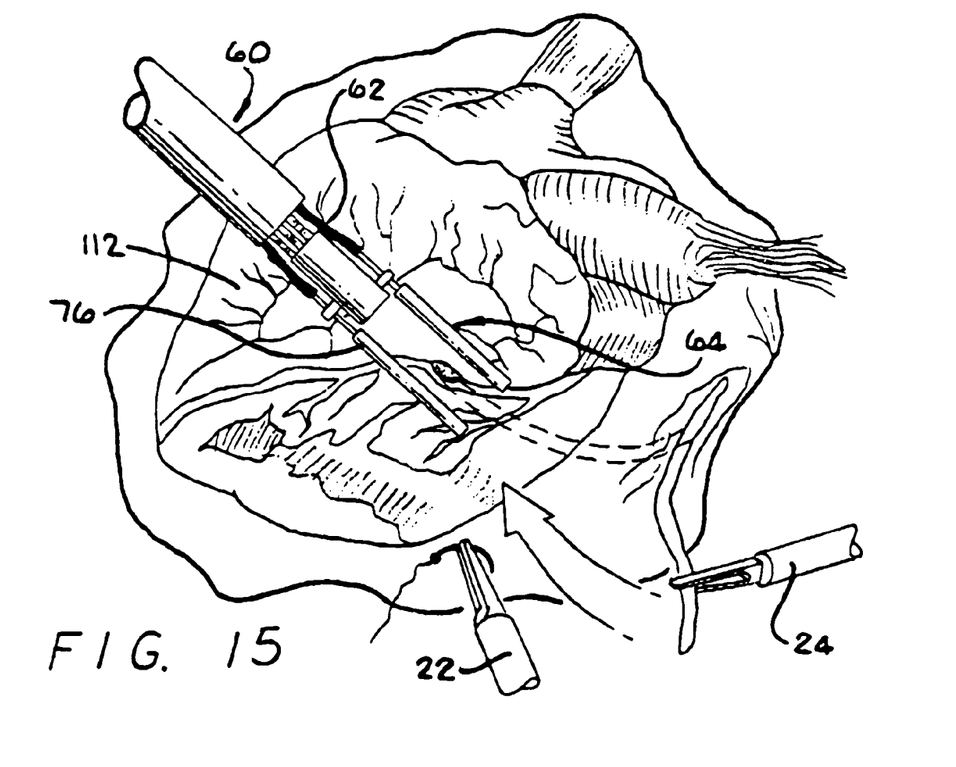
FIG. 15 is a top view showing the heart stabilizer fastened to a heart.
Figure 16:
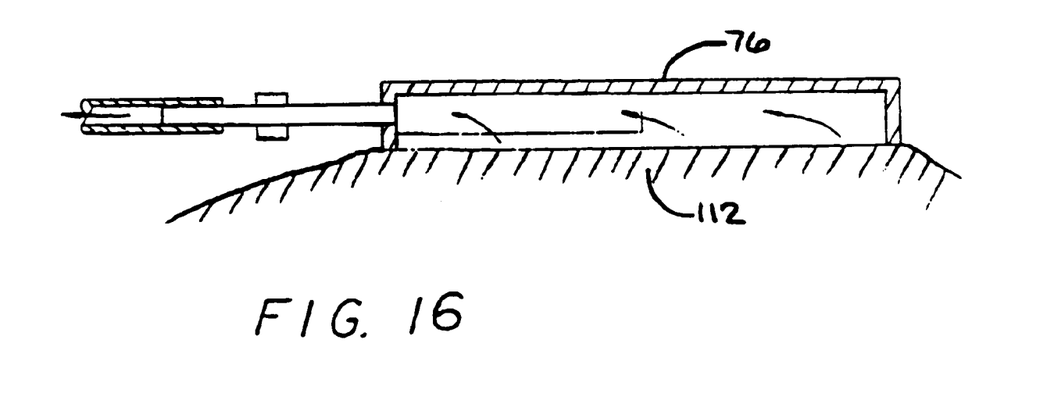
FIG. 16 is a side view of the heart stabilizer fastened to the heart.

As shown in FIGS. 15 and 16, the end effector 64 and wrist 62 can be inserted into the patient's chest cavity adjacent to the heart 112. The surgeon can view the location of the end effector 64 relative to the heart 112 on the monitor 32 shown in FIG. 1. The surgeon can grasp the second linkage 66 and move the stabilizer 60 until the end effector 64 is correctly located on the heart 112. The drive motor can then activated to move the paddles 76 to the desired location. The surgeon may then turn the locking pin to secure the position of the stabilizer 60 relative to the patient.

As shown in FIG. 16, the vacuum source maybe activated to pull the heart 112 into the paddles 76. The stabilizer 60 will then prevent movement of the adjoining area of the heart while the surgeon performs a coronary procedure with the surgical instruments 22 and 24. After the procedure is completed, the stabilizer 60 can be removed by terminating the vacuum and pulling the end effector 64 out of the chest cavity.

Figure 17:
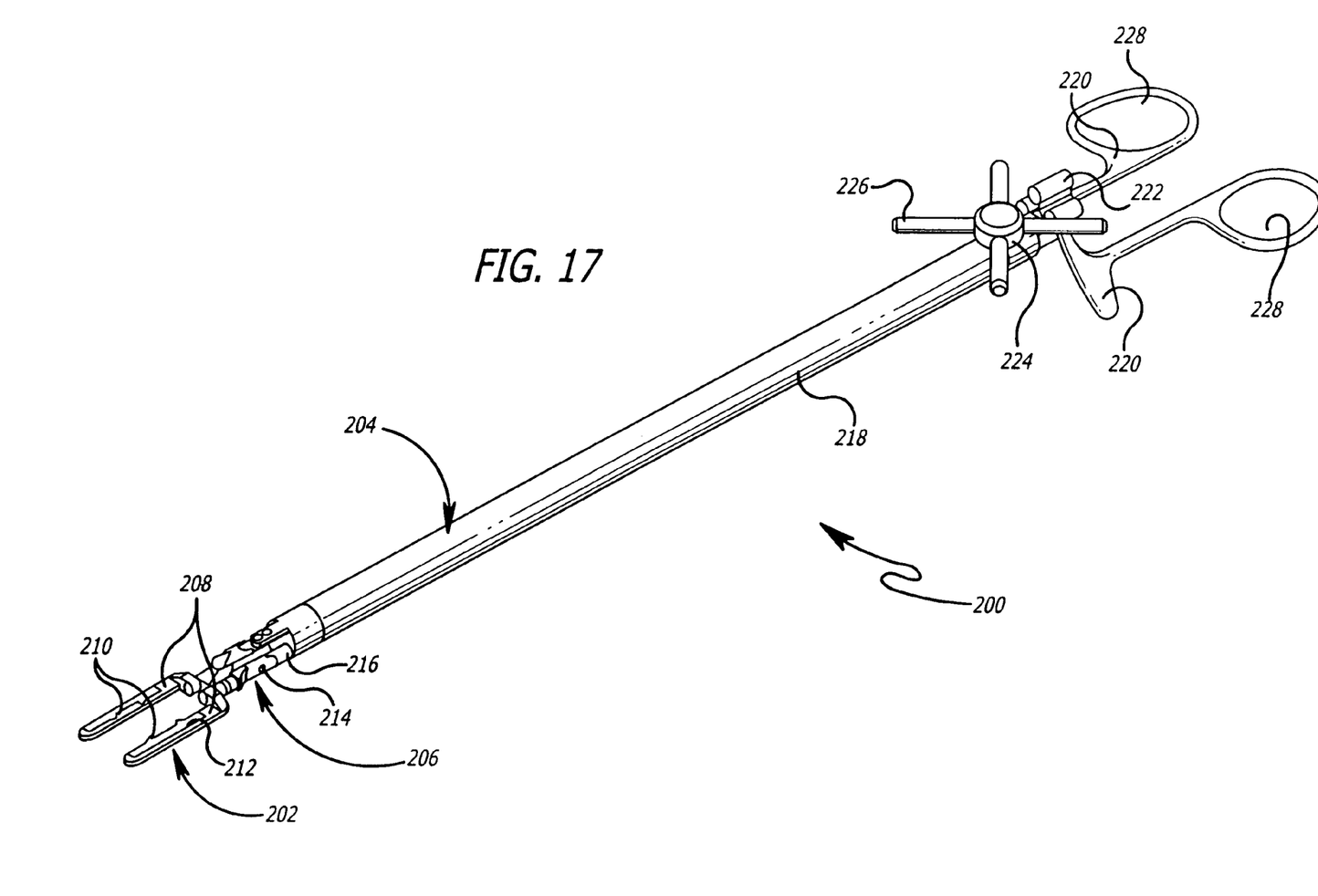
FIG. 17 is a side perspective view of an alternate embodiment of a heart stabilizer.
Figure 18:
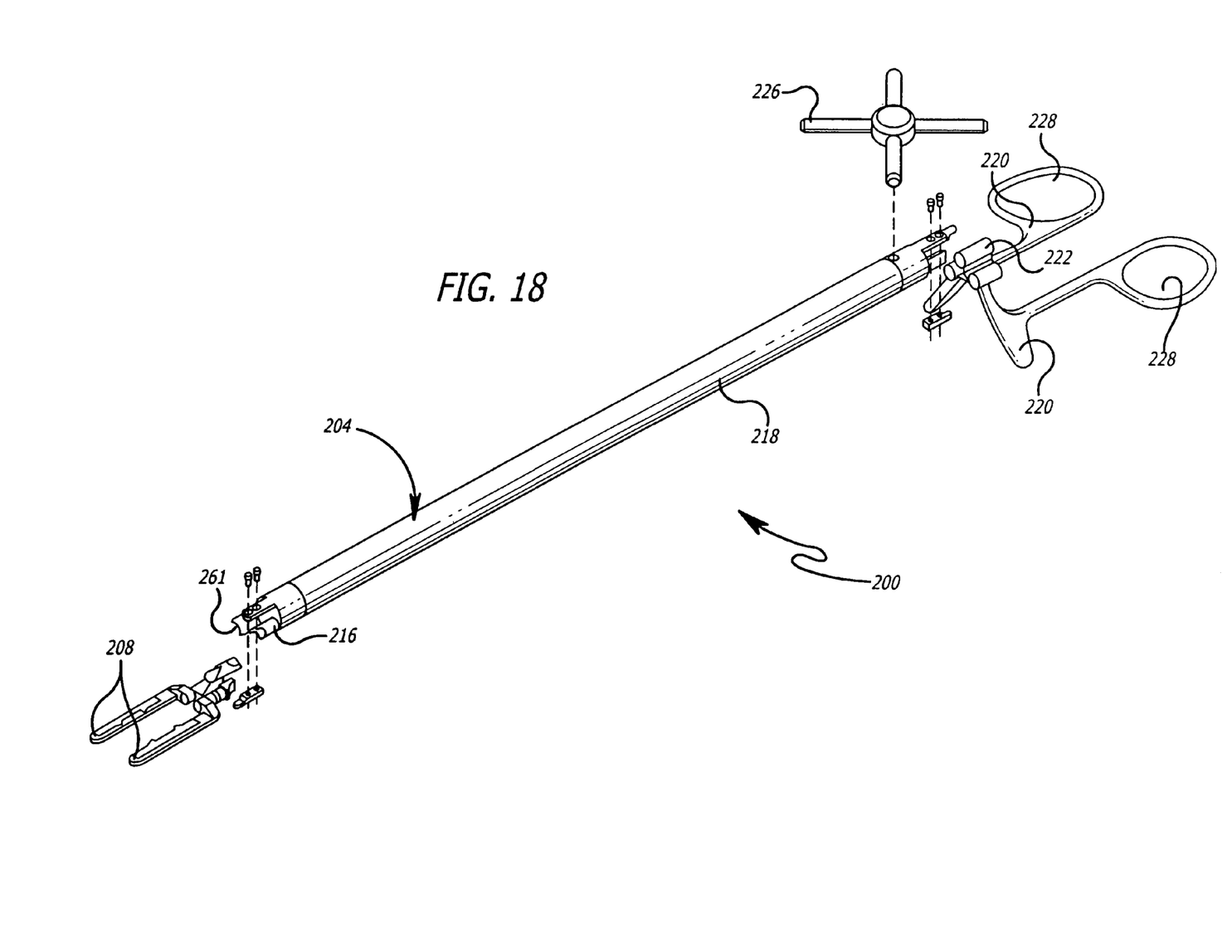
FIG. 18 is an exploded view of the heart stabilizer shown in FIG. 17.

FIGS. 17 and 18 show another embodiment of a heart stabilizer 200 that can be manually operated. The heart stabilizer 200 includes an end effector 202 that is coupled to a first linkage 204 by a wrist 206. The end effector 202 may include a pair of paddles 208. The paddles 208 can be placed onto a beating heart to stabilize the organ. The paddles 208 may have cleats 210 that can anchor sutures used to perform a medical procedure. The sutures can be attached to open wire ends 212 of the cleats 210 during the procedure. For example, sutures are typically used to restrict blood flow during a coronary by-pass procedure. The restricting sutures can be anchored by the cleats 210 and paddles 208 of the stabilizer 200.

The wrist 206 may include an arrangement of universal joints 214 that allow multi-axis rotation of the end effector relative to the first linkage 204. A single universal joint directly couples the end effector 202 to the first linkage 204 to serve as a multi-axis pivot. A sequence of two universal joints 214 couples the shaft of each paddle 208 to its drive shaft 216 that extends through a tube 218 of the linkage 204. An identical sequence of two universal joints (or double universal joint linkage) couples each of the two drive shafts 216 to its respective manually actuated levers 220. The levers 220 can rotate relative to a bracket 222 that is attached to the tube 218. A single universal joint couples the bracket 222 to the first inkage 204, serving as a multi-axis pivot for the bracket 222. Rotation of the levers 220 spins the drive shafts 216, and rotates the paddles 208 between an open position and a closed position. When fully open the paddles 208 contact mechanical stops which prevents further rotation of the levers 220. At this point the levers 220 serve as handle which the operator may use to reorient the bracket 222 assembly relative to the first linkage 204. When such rotation about the bracket 222 pivot universal joint takes place the double universal joint linkages to each driveshaft 216 cause the driveshafts to translate axially relative to the first linkage 204. The double universal joint linkages coupling the driveshafts 216 to the paddle shafts 208 communicate this motion to the end effector 202. The result is that the end effector 202 motion mimics that of the bracket 222. The stabilizer 200 includes a locking pits 224 with a knob 226 that can be rotated by the user to lock and unlock the drive shafts 216 and thereby fix the position of the end effector 202 and paddles 208. The levers 220 may have openings 228 designed to receive fingers of a user.

Figure 19:
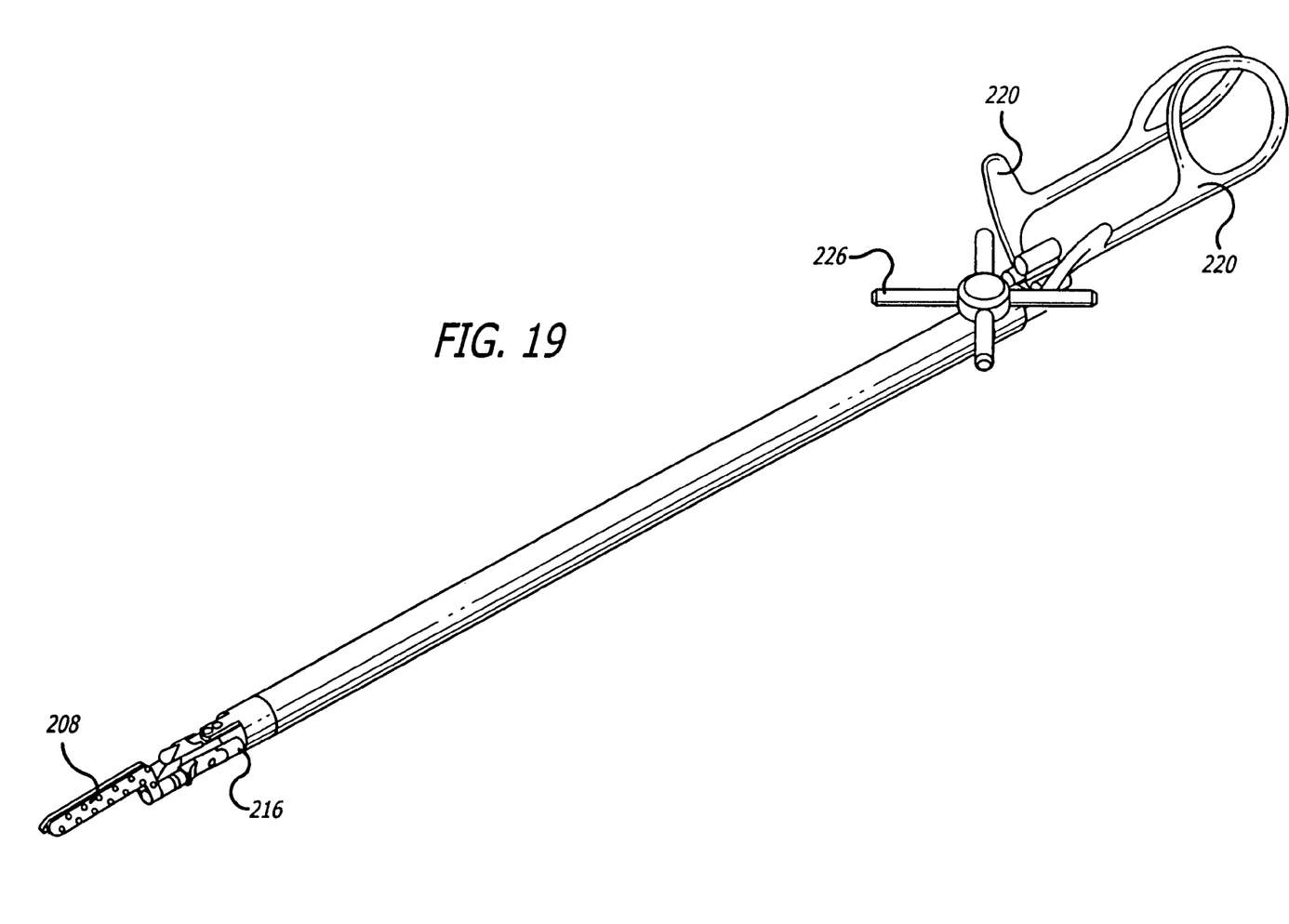
FIG. 19 is a perspective view showing the heart stabilizer of FIG. 17 in a closed position.

In operation, the user rotates the levers 220 to move the paddles 208 into the closed position shown in FIG. 19. The knob 226 is preferably rotated to lock the position of the paddles 208. The stabilizer 200 can then be inserted through a cannula and into an internal cavity of a patient. The knob 226 can be manipulated to unlock the drive shafts 216 so that the levers 220 can be rotated to move the paddles 208 into an open position. Further manipulation of the levers 220 reorients the end effector to the desired position on the heart at which point the knob 226 can be rotated to lock the position of the paddles 208. The entire instrument is then locked in place (relative to the patient) using a static or robotic support arm (not shown). Sutures can be anchored by attachment to the cleats 210 of the paddles 208. When the procedure is completed, the paddles 208 can be moved back to the closed position and the stabilizer 200 can be pulled out of the patient.

As with the previous embodiment, this device may use paddles which employ suction to enhance gripping of the heart tissue. Through suitable modification of the paddles, both embodiments may be used to implement doubly articulating grasping instruments, scissors, clip appliers and other manual instruments. While primarily intended for endoscopic use, all of the instruments described herein are equally suitable for conventional or open surgical procedures. By directly actuating the axial and rotary motions of the driveshafts 216 and eliminating the bracket and levers, robotic versions of all these instrument types can be constructed.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. For example, although the medical devices shown in FIGS. 2–14 and 17–19 has been shown and described as a heart stabilizer, it is to be understood that the devices can be used as a retractor. The paddles 76 and 208 can be used, or modified to be used, as retractor jaws.

What is claimed is:

1. A surgical instrument, comprising:
   a linkage;
   a first shaft extending through the linkage;
   a second shaft extending through the linkage; and
   an end effector;
   wherein the end effector comprises a first paddle and a second paddle, the first and second paddles being substantially parallel;
   wherein the end effector is coupled to the linkage via a first universal joint;
   wherein the first paddle is coupled to the first shaft via a second universal joint;
   wherein the second paddle is coupled to the second shaft via a third universal joint;
   wherein translation of the first shaft, translation of the second shaft, or translation of both the first and the second shaft moves the end effector;
   wherein rotation of the first shaft moves the first paddle; and
   wherein rotation of the second shaft moves the second paddle.

2. The surgical instrument of claim 1, wherein the end effector comprises a heart stabilizer.

3. The surgical instrument of claim 1 further comprising an opening in at least one of the paddles, the opening being configured to provide suction.

4. The surgical instrument of claim 1, wherein the end effector comprises a retractor.

5. The surgical instrument of claim 1, wherein the rotation of the first shaft is motor driven.

6. The surgical instrument of claim 5, wherein the motor is voice activated.

7. The surgical instrument of claim 1, wherein the rotation of the first shaft is manually actuated.

8. The surgical instrument of claim 1, wherein the rotation of the first shaft turns a pinion gear engaged with a rack.

9. The surgical instrument of claim 1 further comprising a locking pin that locks a position of the end effector.

* * * * *